United States Patent [19]

Summers, III et al.

[11] Patent Number: 4,837,190

[45] Date of Patent: Jun. 6, 1989

[54] ORGANIC SOLVENT SOLUBLE POLYVALENT METAL ALKOXY ALKOXIDES

[75] Inventors: William Summers, III, Peekskill; Eric W. Burkhardt, Brewster, both of N.Y.

[73] Assignee: Akzo America Inc., New York, N.Y.

[21] Appl. No.: 861,392

[22] Filed: May 9, 1986

[51] Int. Cl.$^4$ ............................................. B01J 31/02
[52] U.S. Cl. ................................. 502/171; 534/15; 568/678
[58] Field of Search ................ 502/171; 568/678; 534/15

[56] References Cited

U.S. PATENT DOCUMENTS

| | | | |
|---|---|---|---|
| 3,277,002 | 10/1966 | Hunt et al. | 252/32.7 |
| 3,488,303 | 1/1970 | Heims | 260/18 |
| 3,717,666 | 2/1973 | Kobetz et al. | 260/448 AD |
| 3,903,122 | 9/1975 | Thomas | 423/600 X |
| 3,946,102 | 3/1976 | Thomas | 423/600 |
| 4,126,627 | 11/1978 | Reifenberg | 568/851 X |
| 4,330,432 | 5/1982 | Beach et al. | 502/133 X |
| 4,375,564 | 3/1983 | Edwards | 568/678 X |
| 4,634,786 | 1/1987 | Kamienski | 568/678 X |

FOREIGN PATENT DOCUMENTS 2125792  3/1984  United Kingdom ................ 534/15

*Primary Examiner*—Patrick P. Garvin
*Attorney, Agent, or Firm*—Richard P. Fennelly; Louis A. Morris

[57] ABSTRACT

Organic solvent soluble alkoxides of magnesium, calcium, strontium, barium, scandium, yttrium and lanthanum are prepared by the reaction of these elements with alkoxy alcohols.

1 Claim, No Drawings

ORGANIC SOLVENT SOLUBLE POLYVALENT METAL ALKOXY ALKOXIDES

BACKGROUND OF THE INVENTION

Alkoxides of aluminum generally have good solubility in organic solvents. Unfortunately, organic solvent solubility is not a general property of all alkoxides. Alkoxides of polyvalent metals of Groups IIA and IIIA of the Periodic Table, particularly calcium, and magnesium generally have little or no solubility in organic solvents. This relative insolubility is disadvantageous for processes where it is desirable to intimately mix metal containing materials in a mobile liquid phase to achieve a high level of uniformity. Older processes employed physical methods to achieve uniform composition and intimate admixture. For example, synthetic minerals based on oxides of aluminum and magnesium useful as catalyst supports and adsorbents were formed by mixing, sintering, and grinding solid magnesium and aluminum oxides through several process cycles.

U.S. Pats. Nos. 3,903,122 and 3,946,102 describe mixed metal alkoxides having a molar metal proportion of two-thirds aluminum and one-third calcium or magnesium of the general formula:

$$MAl_2(O-CH_2-CH_2-O-R)_8$$

These mixed metal alkoxides are described as soluble in solvents such as benzene.

U.S. Pat. No. 3,717,666 describes alkoxy alcohols used as catalysts in the reaction of alkaline-earth metals with unsubstituted alcohols.

U.S. Pat. No. 4,126,627 mentions (in an apparently prophetic Example, No. 13) the formation of alkali-metal mercaptides from alcohols containing 2-methoxypropyl or 2-butoxypropyl organic groups.

It is desirable to provide organic solvent soluble alkoxides of polyvalent metals which heretofore have been available only as organic solvent insoluble products.

FIELD OF THE INVENTION

This invention relates to the formation of novel alkoxides, methods of making such alkoxides, and processes of using said alkoxides.

DETAILED DESCRIPTION OF THE INVENTION

Metal alkoxides (also called metal alcoholates) are compounds having a metal attached to alkyl groups by an oxygen atom. Many alkoxides of polyvalent metals are industrially important, for example, the organic solvent soluble alkoxides of "metals" such as aluminum, silicon, titanium, and zirconium.

Alkoxides of Group IIA and Group IIIA of the Periodic Table generally do not have appreciable organic solvent solubility. For example, magnesium ethylate and calcium methylate are essentially insoluble in organic solvents. This property of low organic solvent solubility limits industrial applications.

Compounds of the Invention

It is a discovery of this invention that alkoxides of Group IIA and Group IIIA metals having at least one alkoxy alkoxide group are generally organic solvent soluble. In particular, Group IIA and Group IIIA metal alkoxides having only alkoxy alkoxide groups are generally highly organic solvent soluble.

This disclosure defines Group IIA metals as inclusive of magnesium, calcium, strontium, and barium. Group IIIA metals are defined as inclusive of scandium, yttrium, and lanthanum. The defining characteristic of an alkoxide being "organic solvent soluble" is defined herein to be a solubility of at least 15 weight percent at ambient (approx. 20° C.) temperature in toluene or 2-methoxy ethanol or 2-butoxy butanol.

The alkoxides of this invention are novel compounds represented by the following formulae:
$(Z-(CH_2)_n-O)-Mg-(O-(CH_2)_m-OR_2)$ and
$(Z-(CH_2)_n-O)-Ca-(O-(CH_2)_m-OR_2)$ and
$(Z-(CH_2)_n-O)-M2-(O-(CH_2)_m-OR_2)$ and $$(Z-(CH_2)_n-O)-M3-(O-(CH_2)_m-OR_2)$$
$$|$$
$$(O-(CH_2)_p-Z)$$

wherein M2 is a Group IIA metal selected from strontium or barium; M3 is a Group IIIA metal selected from scandium, yttrium or lanthanum; m, n and p are the same or different positive integers from 1 to 12; Z is $(R_1O)-$ or $(R_1)-$ and $R_1$ and $R_2$ are the same or different hydrocarbyl radicals of from 1 to 20 carbon atoms.

The metal alkoxy alkoxides of this invention are conveniently prepared in such a manner that the alkoxy akoxide moieties are the same. These alkoxides may be represented by the formulae:
$Mg(O-(OCH_2)_n-OR_1)_2$
$Ca(O-(CH_2)_n-OR_1)_2$
$Sr(O-(CH_2)_n-OR_1)_2$
$Ba(O-(CH_2)_n-OR_1)_2$
$Sc(O-(CH_2)_nOR_1)_3$
$Y(O-(CH_2)_n-OR_1)_3$
$La(O-(CH_2)_n-OR_1)_3$
where n and $R_1$ are as previously defined.

Mixtures containing any combination of the metal alkoxy alkoxides represented in the preceding two paragraphs are also within the scope of this invention.

Particularly preferred $R_1$ groups are those with one to four carbon atoms, such as methyl, ethyl, propyl, and butyl. Examples of specific alkoxides of this invention are as follows:

Magnesium bis (2-methoxyethylate)
Magnesium bis (2-ethoxyethylate)
Magnesium bis (2-butoxyethylate)
Magnesium bis (3-methoxypropylate)
Magnesium bis (3-ethoxypropylate)
Magnesium bis (3-propoxypropylate)
Magnesium bis (3-methoxybutylate)
Calcium bis (2-methoxyethylate)
Calcium bis (2-ethoxyethylate)
Calcium bis (2-butoxyethylate)
Calcium bis (3-methoxypropylate)
Calcium bis (3-ethoxypropylate)
Calcium bis (3-butoxypropylate)
Calcium bis (3-methoxybutylate)
Strontium bis (2-methoxyethylate)
Strontium bis (2-ethoxyethylate)
Strontium bis (3-methoxybutylate)
Barium bis (2-methoxyethylate)
Barium bis (2-ethoxyethylate)
Lanthanum tris (2-methoxyethylate)
Lanthanum tris (2-ethoxyethylate)
Lanthanum tris (2-methoxybutylate)

Scandium tris (2-methoxyethylate)
Scandium tris (2-ethoxyethylate)
Scandium tris (3-methoxybutylate)
Yttrium tris (2-methoxyethylate)
Yttrium tris (2-ethoxyethylate)
Yttrium tris (2-butoxyethylate)
Yttrium tris (3-methoxypropylate)
Yttrium tris (3-ethoxypropylate)
Yttrium tris (3-propoxypropylate)
Yttrium tris (3-methoxybutylate)
Yttrium tris (3-butoxybutylate)
or mixtures of the above compounds.

The metal alkoxy alkoxides are organic solvent soluble liquids or solids. These compounds are generally reactive with atmospheric oxygen and moisture and should be stored in a protected environment.

Method of Making Alkoxy Alkoxides

The alkoxides of magnesium, calcium, strontium, yttrium and lanthanum are synthesized by reacting these elements as metals directly with an alkoxy alcohol containing alcohol reactant.

The alkoxy alcohol containing alcohol reactant may itself constitute the reaction medium. Alternatively, an unreactive aromatic, aliphatic, or cycloaliphatic diluent such as toluene, octane, cyclohexane, or mixtures thereof may be used as reaction medium.

The alkoxy alcohol containing alcohol reactant may be entirely composed of alkoxy alcohol or may be a mixture of alkoxy alcohols with simple alcohols. Simple alcohols are alcohols reactive with Group IIA or Group IIIA metals, said simple alcohols being represented by the formula:

$$R_1\text{---OH}$$

wherein $R_1$ is a hydrocarbyl group of from 1 to 20 carbon atoms. Preferably $R_1$ is an alkyl group of from 1 to 4 carbon atoms. Useful $R_1$ groups include ethyl, propyl and butyl.

Illustrative simple alcohols are ethanol, propanol, isopropanol, and n-butanol.

The alkoxy alcohol component of the alcohol reactant is represented by the formula:

$$\text{HO---(CH}_2)_m\text{---OR}_1$$

wherein m is a positive integer from 1 to 12 and $R_1$ is a hydrocarbyl group having 1 to 20 carbon atoms. Preferably, m has a value from 1 to 4 and $R_1$ is an alkyl group of from 1 to 12 carbon atoms. Useful alkoxy alcohols include the following:
2-methoxy ethanol
2-ethoxy ethanol
2-butoxy ethanol
3-methoxy propanol
3-ethoxy propanol
3-propoxy propanol
3-butoxy propanol
3-methoxy butanol The molar proportions of (1) metal reactant and alkoxy alcohol containing alcohol reactant are not critical. Approximately stoichiometric proportions of the reactants may be used, for example, two moles of alcohol reacted with one mole of Group IIA metal or three moles of alcohol reacted with one mole of Group IIIA metal.

It is an essential aspect of this invention to have an amount of alkoxy alcohol in the alcohol reactant that on the average replaces at least one bond of the Group IIA or Group IIIA metal with an alkoxy alcohol moiety. The balance of the alkoxy alcohol containing alcohol reactant may be a simple alcohol reactive with the Group IIA or Group IIIA metal selected. Preferably, at least one-half of the moles of alcohol in the alcohol containing reaction are alkoxy alcohol. Most preferably, the alkoxy alcohol containing alcohol reactant is substantially completely composed of one or more alkoxy alcohols.

It is usually preferred to have an excess of alkoxy alcohol containing alcohol reactant to remove the solid metal reactant from the reaction medium and make subsequent processing of the alkoxide product easier. The alcohol reactant is present in the reaction medium most preferably in a molar proportion equivalent to at least 110 percent of the stoichiometric requirements of the metal.

The reaction medium may be a mixture of an inert solvent and liquid alcohol. For example, a mixture of toluene and 2-methyoxy ethanol may be employed.

The temperature of reaction is not critical and typically ranges from the ambient temperatures up to the boiling point of the reaction medium.

Completion of the reaction may be determined by cessation of hydrogen gas evolution. Typically, the formation of the Group IIA and Group IIIA alkoxy alkoxides is substantially completed in ½ to 12 hours.

Preliminary purification of the reaction product is often not necessary in many instances since the product is in a useful solution form where it can be coprocessed with other materials. However, if desired, the alkoxy alkoxides of this invention may be separated from their reaction medium by a variety of techniques such as solvent stripping, solvent extraction and recrystallization.

One or more metal alkoxy alkoxides of the invention may be formed in the same reaction. For example, metallic calcium and magnesium may be placed in a reaction medium with a suitable alkoxy alcohol containing alcohol reactant. Moreover, the Group II and Group III metals may be mixed with other metals known to form soluble alkoxides. For example, the elements aluminum, titanium, silicon, vanadium, and zirconium or mixtures thereof may be simultaneously reacted with calcium, magnesium, strontium, barium, scandium, yttrium, or lanthanum to give mixtures of soluble alkoxy alkoxides.

A catalyst may be used to assist the reaction rate and yield of the above method. Catalysts such as iodine or mercuric chloride are of use in the method of the invention.

Homogeneous Liquid Compositions of the Invention

Useful compositions contain as essential ingredients: (1) one or more Group IIA or Group IIIA metal alkoxy alkoxides, (2) one or more organic solvent soluble hydrolyzable metal compounds of aluminum, silicon, titanium, or zirconium, and (3) an organic solvent.

The ingredient (1) Group IIA or Group IIIA metal alkoxy alkoxide has been previously defined. The ingredient (2) compounds of aluminum, silicon, titanium, vanadium, or zirconium may be alkoxy alkoxides or simple alkoxides derivable from the ingredient (2) metals with primary, secondary or tertiary alcohols represented by the formula:

$$R_1-OH$$

wherein $R_1$ is an alkyl group or alkoxy alkyl of from 1 to 20 carbon atoms. Exemplary ingredient (2) alkoxides include:
aluminum isopropylate
aluminum sec-butylate
tetraisopropyl titanate
tetrabutyl titanate
zirconium tetra-n-propylate
zirconium tetra-n-butylate
vanadium butylate
tetra-n-propyl silicate
tetraethylsilicate The ingredient (3) organic solvent is a alkoxide non-reactive liquid that is capable of dissolving at least 20 percent by weight of either alkoxide ingredients (1) or (2).

Useful solvents include the following:
2-methoxy ethanol
2-ethoxy ethanol
2-methoxy propanol
2-ethoxy propanol
2-propoxy propanol
2-butoxy propanol
cyclohexane
toluene
heptane
octane Solutions of metal alkoxy alkoxides are formed by contacting with agitation the solvent and alkoxide. The mixed alkoxide liquid composition containing soluble Group IIA and Group IIIA metals is useful as a starting material for forming mixed metal oxide/hydroxide catalyst supports, molecular sieves, and adsorbents.

A general procedure for utilizing the liquid compositions of mixed alkoxides is to hydrolyze the soluble alkoxides of this invention to form a uniform and homogeneous precipitate, then dry the precipitate to form a high purity mixed metal oxide product. Details of a suitable hydrolysis and preparative procedure are given in Columns 3 and 4 of U.S. Pat. No. 3,946,102; the disclosure of which is incorporated herein by reference.

The method and composition of the invention are illustrated in the following examples:

EXAMPLE 1

This Example illustrates the synthesis of $Mg(OCH_2CH_2OCH_3)_2$.

Magnesium metal (12.15g) was placed in a flask with toluene (220ml). After heating to 70° C., 2-methoxy ethanol (96ml) was added very slowly to control the effervescence of hydrogen. The mixture was then cooled to ambient temperature, and filtered to remove a small amount of black precipitate. The resultant alkoxide solution had no insoluble material after storage for more than two weeks. Evaporation of the solvent yielded the solid magnesium alkoxide in 96% yield. The compound is very soluble in methanol, ethanol, toluene, and 2-methoxy ethanol.

EXAMPLE 1A

This Example illustrates the synthesis of $Mg(OCH_2CH_2)CH_2CH_3)_2$. The general procedure of Example 1 is followed except 118 ml. of 2-ethoxyethanol is used. Evaporation of solvent yielded the solid magnesium alkoxide in 96% yield. The compound is soluble in toluene (20%), ethoxyethanol (18%) and insoluble in aliphatic hydrocarbons.

EXAMPLE 1B

This Example illustrates the synthesis of $Mg(OCH_2CH_2OCH_2CH_2CH_2CH_3)_2$. The general procedure of Example 1 is followed except 131 ml. of 2-butoxyethanol is used. Evaporation of solvent yielded a semi-solid magnesium alkoxide in 94% yield. The compound is soluble in toluene (20%), butoxyethanol (40%) and heptane (35%).

EXAMPLE 1C

This Example illustrates the synthesis of $Mg(OCH_2CH_2CH(OCH_3)CH_3)_2$. The general procedure of Example 1 is followed except 112 ml. of 3-methoxy butanol is used. Evaporation of solvent yielded the solid magnesium alkoxide in near quantitative yield. The compound is soluble in methanol (5%), isopropanol (5%), ethanol (5%), methoxyethanol (20%), ethoxyethanol (20%), toluene (10%) and only slightly soluble in n-octane (<1%).

EXAMPLE 1D

This Example illustrates the synthesis of $Mg(OCH_2CH_3)(OCH_2CH_2OCH_2CH_2CH_2CH_3)$. The general procedure of Example 1 is followed except heptane is used instead of toluene and an alcohol mixture consisting of 30 ml. ethanol and 65 ml. 2-butoxy ethanol is used. Evaporation of the solvent yielded a semi-solid magnesium alkoxide in 88% yield. The compound is soluble in toluene (35%) and heptane (35%).

EXAMPLE 1E

This Example illustrates the synthesis of $Mg(OCH_2CH(OCH_3)CH_3)_2$. The general procedure of Example 1 is followed except than 110 ml. of propylene glycol methylether is used. Evaporation of solvent yielded a solid magnesium alkoxide in 85% yield. The compound is soluble in toluene (30%) and propylene glycol methylether (30%).

EXAMPLE 2

This Example illustrates the preparation of a magnesium/aluminum alkoxide spinel precursor.

Magnesium 2-methoxyethylate (16g from the synthesis of Example 1) and aluminum sec-butoxide (45g) were refluxed with 2-methoxyethanol (150ml) for 15 minutes. The resulting solution was cooled, and stripped under vacuum, yielding a viscous clear oil.

EXAMPLE 3

This Example describes the preparation of a magnesium/aluminum/silicon alkoxide cordierite precursor.

The Mg/Al alkoxide spinel from Example 2 (43G) was mixed with tetraethylsilicate (27.5g). The components were completely miscible, forming a clear solution.

EXAMPLE 4

This Example illustrates the synthesis of $Y(OCH_2CH_2OCH_3)_3$.

Yttrium metal (15g) was suspended in toluene (200 ml). The mixture was heated to reflux, and 2-methoxyethanol (80 g) was added dropwise. Reflux was maintained for three hours after the addition was completed, whereupon more 2-methoxyethanol (80 g) was charged to the mixture. After another three hours at reflux, the mixture was cooled and filtered through CELITE filter aid. The filtrate was stripped to dryness yielding a very viscous light brown oil. The alkoxide is soluble in toluene as well as the parent alcohol.

EXAMPLE 5

This Example illustrates the synthesis of $Ba(OCH_2CH_2OCH_3)$. Barium metal shot (22.3 g) was placed into a flask with toluene (150 ml). The toluene was brought to reflux followed by the slow addition of 2-methoxyethanol (50 ml). After the hydrogen ceased, the reaction mixture was allowed to cool to room temperature and was filtered yielded a brown colored filtrate. The volatiles were removed from the filtrate to yield a brown oil. The resultant oil remained in this state for more than 2 weeks without any solid precipitating out.

EXAMPLE 6

Preparation of lanthanum alkoxyalkoxide

This Example has two parts. Part A describes an attempted synthesis outside the scope of the invention. Part B describes the formation of lanthanum alkoxyalkoxides within the scope of this invention.

Part A 10 grams of lanthanum metal were suspended in 250 cc of ethanol. The reaction mixture was refluxed for 8 hours. At the end of the reflux there was no evidence of reaction.

Part B

The ethanol was distilled off from the reaction mixture of Part A. 250 cc of methoxyethanol were added and the reaction mixture heated to reflux. The reflux evidenced such evolution of hydrogen and was continued for 24 hours. The brown product was filtered and the filtrate stripped. A viscous oil remained. The oil product analysis was 18 grams of $La(OCH_2CH_2OCH_3)_3$. The reaction product was dissolved in toluene to give a 21% by weight solution.

EXAMPLE 7

Preparation of a calcium alkoxyalkoxide 25 grams of calcium metal were milled in a ball mill for 8 hours with 875 grams of stainless steel balls and 0.1 gram of $HgCl_2$. 7.3 grams of milled calcium metal were recovered.

The calcium metal (0.18 moles) was added to 250 cc of methoxyethanol over a 30-minute period and heated to reflux temperature. The mixture evidenced vigorous hydrogen evolution upon the calcium metal addition. The reflux was continued for 6 hours and the reaction product then filtered to remove unreacted metal. The resulting filtrate had a dark color which became darker upon standing. The filtrate was then stripped and 32.6 (34.2 theoretical yield) grams of a dark viscous oil remained.

We claim:

1. A composition comprising as essential ingredients: (i) a solvent; (ii) a yttrium alkoxy alkoxide; and (iii) a zirconium alkoxide.

* * * * *